US00PP33328P2

(12) United States Plant Patent
Olesen

(10) Patent No.: US PP33,328 P2
(45) Date of Patent: Aug. 10, 2021

(54) FLORIBUNDA ROSE PLANT NAMED 'POULPAL087'

(50) Latin Name: *Rosa hybrida*
Varietal Denomination: Poulpal087

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/974,002

(22) Filed: Sep. 3, 2020

(51) Int. Cl.
*A01H 5/02* (2018.01)
*A01H 6/74* (2018.01)

(52) U.S. Cl.
USPC ..... Plt./144

(58) Field of Classification Search
USPC ..... Plt./101, 141, 144
See application file for complete search history.

*Primary Examiner* — Susan McCormick Ewoldt

(57) ABSTRACT

A new garden rose plant of the Compact Floribunda class which has abundant, near white flowers and attractive foliage. This new and distinct variety has shown to be uniform and stable in the resulting generations from asexual propagation.

2 Drawing Sheets

Botanical designation: *Rosa hybrida.*
Variety denomination: 'Poulpal087'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulpal087', originated as a single seedling from the stated cross.

The new variety may be distinguished from its male pollen parent and female seed parent primarily by the following characteristics. The male pollen parent plant has orange white flowers while the new variety has near white flowers with intonations of green white. The female seed parent plant has apricot flowers while the new variety has near white flowers.

The objective of the hybridization of this rose variety was to create a new and distinct variety with unique qualities, such as:

1. Uniform and abundant near white flowers;
2. Vigorous, but compact growth when propagated on its own roots;
3. Exceptional disease resistance.

This combination of qualities is not present in previously available commercial cultivars of this type, known to the inventor, and distinguish 'Poulpal087' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulpal087' was selected in the spring of 2014 by the inventor as a single plant from the progeny of the aforementioned hybridization.

Asexual reproduction of 'Poulpal087' by rooted cuttings was first done by Mogens N. Olesen in the nursery in Fredensborg, Denmark in July, 2014. This initial and other subsequent asexual propagations conducted in controlled environments have demonstrated that the characteristics of 'Poulpal087' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal087'.

Specifically illustrated in FIG. 1 of the drawings are open flowers viewed from above and from the side, sepals and petals detached revealing reproductive flower parts and receptacle.

Figure 1:
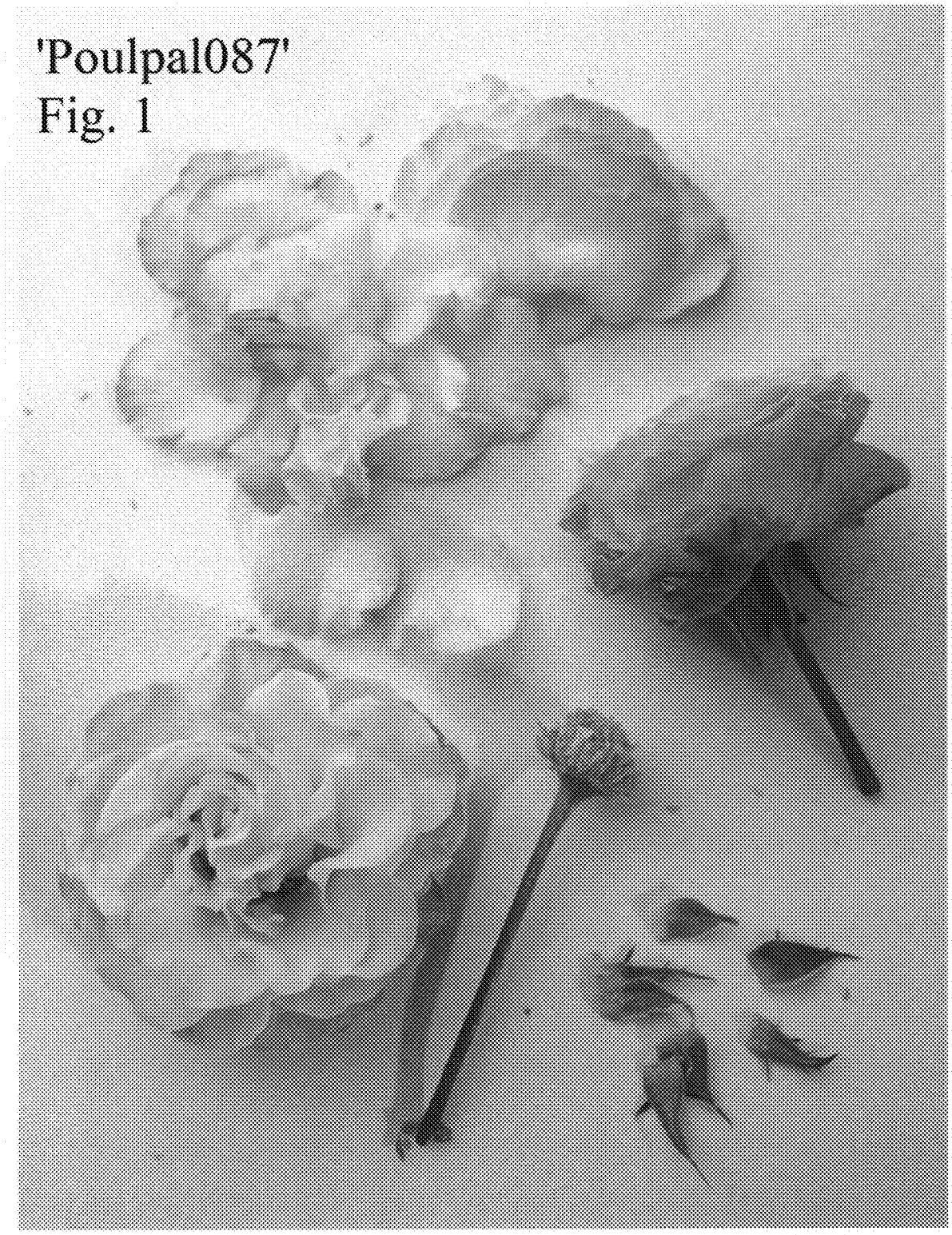
Figure 2:
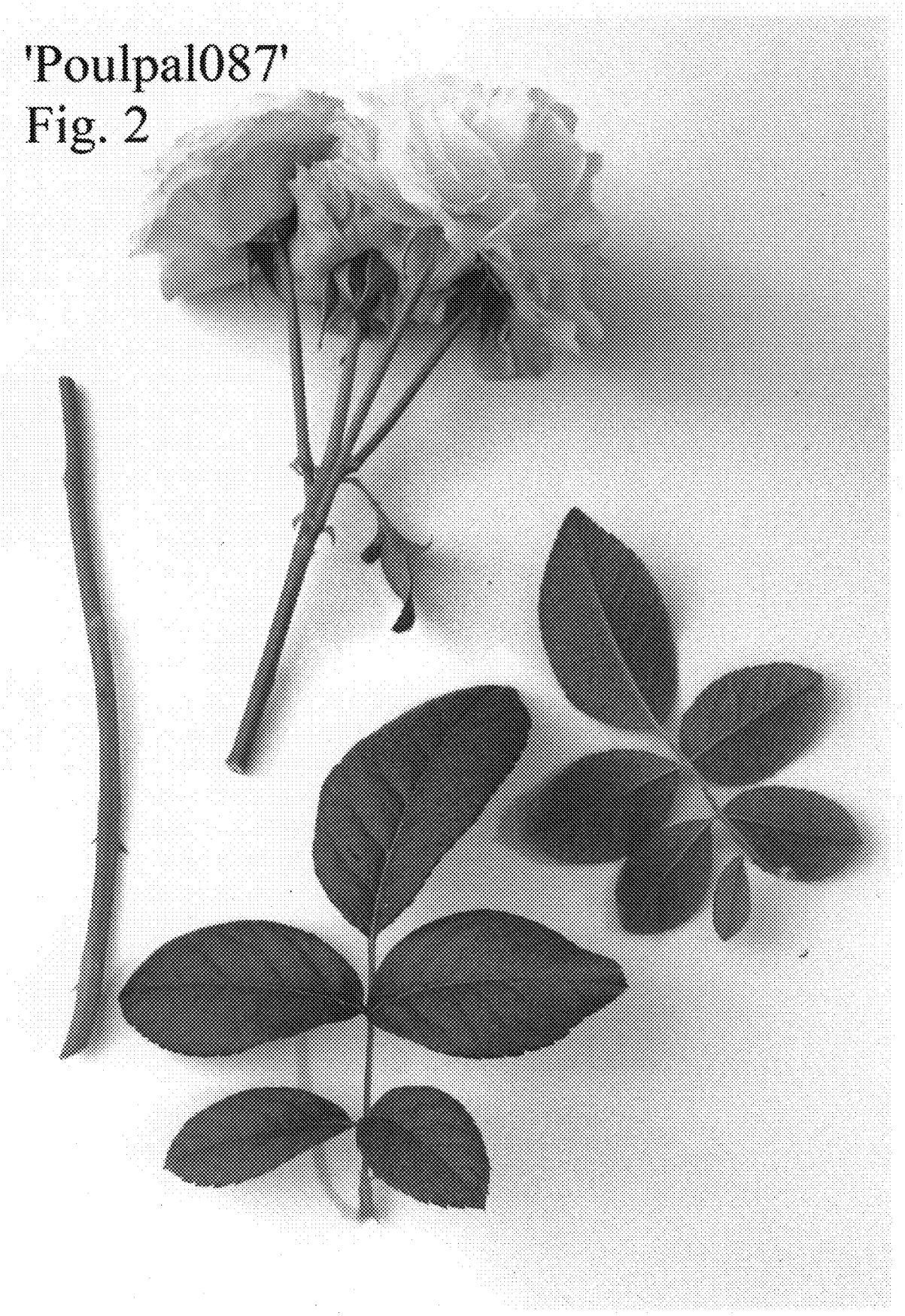

Specifically illustrated in FIG. 2 of the drawings is a cluster of open flowers on the branch, bare stems and leaves. Plants shown are 4 months of age.

DETAILED DESCRIPTION OF THE VARIETY

The following is a description of 'Poulpal087', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpah051', U.S. Plant Pat. No. 24,222 are compared to 'Poulpal087' in Chart 1.

CHART 1

| | 'Poulpal087' | 'Poulpah051' |
|---|---|---|
| Petal Count | 45 | 50 |
| Flower Diameter | 70 mm | 35 to 40 mm |
| Petal color, upper side outer petals | Yellow-Green Group 145D at margins. Middle and basal zone are White Group 155B. At the point of attachment Yellow Group 3C | Green-White Group 155C with intonations of Yellow-Green Group 145C at the margins |

FLOWER AND FLOWER BUD

Blooming habit: Continuous.

Flower bud:

*Size*.—Upon opening, 25 mm in length from base of receptacle to end of bud. Bud diameter is 19 mm.

*Bud form*.—Ovoid.

*Sepal inner surface*.—Color: Yellow-Green Group 146D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—23 mm long, 10 mm wide.

*Receptacle*.—Texture: Smooth. Size: 4 mm in height, 9 mm wide. Color: Yellow-Green Group 144A. Shape: Funnel.

*Pedicel*.—Surface: Smooth. Length: 65 mm. Diameter: 3 mm on average. Color: Yellow-Green Group 144A. Strength: Strong.

Flower bud development: Flower buds are borne single or in clusters of about 5 flower buds per stem.

Flower bloom:

*Fragrance*.—Light floral scent.

*Duration*.—The blooms have a duration on the plant of approximately 19 days. Petals fall cleanly away from plant after flowers have fully matured.

*Size*.—Flower diameter is 70 mm when open. Flower depth is 31 mm.

*Flower shape*.—Rosette very double flower with many slightly overlapping petals of different sizes.

*Shape of flower, side view*.—The upper portion is flat. The lower portion is concave.

Petalage: Under normal conditions, flowers have about 45 petals.

General tonality of flower: Open flowers are Yellow-Green Group 150D.

Petal color:

*Upon opening, outer petals*.—Upper surface: Yellow-Green Group 145D at margins. Middle and basal zone are White Group 155B. At the point of attachment Yellow Group 3C. Lower surface: Yellow-Green Group 145C. No distinctive coloration at the base.

*Upon opening, inner petals*.—Upper surface: White Group 155B shaded with Yellow Group 2C at the middle and basal zone. Lower surface: White Group 155B shaded with Yellow Group 2C at the middle and basal zone.

*After opening, outer petals*.—Upper surface: Yellow-Green Group 145D at margins. Middle and basal zone are White Group 155B. At the point of attachment Yellow Group 3C. Lower surface: Yellow-Green Group 145C. No distinctive coloration at the base.

*After opening, inner petals*.—Upper surface: White Group 155B shaded with Yellow Group 2C at the middle and basal zone. Lower surface: White Group 155B shaded with Yellow Group 2C at the middle and basal zone.

Petals:

*Petal reflex*.—Somewhat reflexed.

*Margin*.—Entire and uniform. Strong undulations.

*Shape*.—Broad and round. Apex shape: Rounded. Base shape: Obtuse.

*Size*.—32 mm (l)×36 mm (w).

*Texture*.—Smooth.

*Thickness*.—Above average.

Reproductive flower parts:

*Pollen*.—None observed.

*Anthers*.—Size: 2 mm in length. Color: Yellow Group 2D. Quantity: 65 on average.

*Filaments*.—Color: Yellow Group 2D. Length: 5 mm.

*Pistils*.—Length: 9 mm. Quantity: 35 on average.

*Stigmas*.—Color: Yellow Group 6C.

*Styles*.—Color: Yellow-Green Group 145D.

*Location of stigmas*.—Superior in location relative to the length of the filaments and the height of the anthers.

*Hips*.—None Observed.

PLANT

Plant growth: Upright and compact. Plants are 35 cm in height, and 30 cm wide.

Stems:

*Color of juvenile growth*.—Yellow-Green Group 144B.

*Color of mature growth*.—Yellow-Green Group 144A.

*Length*.—Canes are about 19 cm from the base of the plant to the flowering portion.

*Diameter*.—About 5 mm.

*Internodes*.—On mature canes about 45 mm between nodes.

*Surface texture*.—Young wood: Smooth. Older wood: Smooth.

Long prickles:

*Incidence*.—4 prickles per 10 cm of stem.

*Size*.—Average length of prickles on mature stems is 3 mm.

*Shape*.—Upper portion is linear. Lower portion is concave.

*Color*.—Juvenile prickles: Greyed-Orange Group 174C. Mature prickles: Greyed-Orange Group 174C.

Plant foliage:

*Compound leaf*.—140 mm (l)×110 (w).

*Quantity*.—2 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 12 mm long, mm wide. Quantity: 2 per compound leaf Shape: Linear, slightly broad based with outward extending apices. Margins: Finely serrated. Color:

*Petiole*.—Length: About 21 mm. Diameter: 2 mm. Upper surface color: Yellow-Green Group 144A. Lower surface color: Yellow-Green Group 144A.

*Rachis*.—Length: About 43 mm. Upper surface color: Yellow Green Group 144A. Lower surface color: Yellow-Green Group 144A.

*Leaflet*.—Quantity: Normally 5 leaflets. Margins: Serrated. Size: Terminal leaflets are about 65 mm long, 45 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal087', substantially as illustrated and described herein, due to its abundant near white flowers, disease resistance, and extended period of bloom.

* * * * *

'Poulpal087'

'Poulpal087'